United States Patent
Wu et al.

(10) Patent No.: US 10,272,063 B2
(45) Date of Patent: *Apr. 30, 2019

(54) TREATMENT FOR ISCHEMIC STROKE

(71) Applicant: CHS Pharma, Inc., Miami, FL (US)

(72) Inventors: Jang-Yen Wu, Boca Raton, FL (US); Howard Malcolm Prentice, Boca Raton, FL (US)

(73) Assignee: CHS Pharma, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/803,280

(22) Filed: Nov. 3, 2017

(65) Prior Publication Data

US 2018/0055809 A1    Mar. 1, 2018

Related U.S. Application Data

(63) Continuation of application No. 14/731,783, filed on Jun. 5, 2015, now Pat. No. 9,827,220, which is a continuation of application No. 13/853,183, filed on Mar. 29, 2013, now Pat. No. 9,050,305.

(60) Provisional application No. 61/617,276, filed on Mar. 29, 2012.

(51) Int. Cl.
| | | |
|---|---|---|
| *A61K 45/00* | (2006.01) | |
| *A61K 38/00* | (2006.01) | |
| *A01N 37/18* | (2006.01) | |
| *A61K 31/27* | (2006.01) | |
| *A61K 38/19* | (2006.01) | |
| *A61K 31/192* | (2006.01) | |

(52) U.S. Cl.
CPC ............ *A61K 31/27* (2013.01); *A61K 31/192* (2013.01); *A61K 38/193* (2013.01); *A61K 2300/00* (2013.01)

(58) Field of Classification Search
None
See application file for complete search history.

(56) References Cited

U.S. PATENT DOCUMENTS 6,156,794 A * 12/2000 Faiman ................. A61K 31/145
                                                      514/478
9,827,220 B2 * 11/2017 Wu ....................... A61K 38/193

OTHER PUBLICATIONS

Chapman et al., Stroke, 2000, 31:2920-4.*

* cited by examiner

*Primary Examiner* — Olga N Chernyshev
(74) *Attorney, Agent, or Firm* — Stanley A. Kim

(57) ABSTRACT

Granulocyte colony-stimulating factor (G-CSF; a stem cell enhancer and facilitator), DETC-MeSO (a glutamate receptor partial antagonist and anti-excitotoxicity agent), and sulindac (a potent anti-oxidant and anti-inflammatory agent) each can protect brain tissue exposed to a cerebral ischemia/reperfusion injury, and minimize the size of infarcts that develop as a result of the injury. When administered in combination, these agents are effective at protecting brain tissue and minimizing the size of an infarct resulting from the injury at much lower concentrations compared to using a single agent.

11 Claims, No Drawings

TREATMENT FOR ISCHEMIC STROKE

CROSS-REFERENCE TO RELATED APPLICATIONS

This application is a continuation application of U.S. patent application Ser. No. 14/731,783 filed on Jun. 5, 2015, which is a continuation application of U.S. patent application Ser. No. 13/853,183 filed on Mar. 29, 2013 (now U.S. Pat. No. 9,050,305), which claims priority from U.S. provisional patent application No. 61/617,276 filed on Mar. 29, 2012.

STATEMENT AS TO FEDERALLY SPONSORED RESEARCH

Not applicable.

FIELD OF THE INVENTION

The invention relates generally to the fields of neurology, pharmaceuticals, and medicine. More particularly, the invention relates to the use of agents to protect brain tissue from ischemia/reperfusion injury.

BACKGROUND

Stroke is the leading cause of disability and the third leading cause of death in the USA. Much progress has been made regarding the mechanism of brain injury induced by ischemia/hypoxia, a major pathophysiology of stroke. It is generally believed that excitotoxicity caused by excessive release of excitatory neurotransmitter glutamate plays an important role in ischemia/reperfusion induced neuronal death. Despite extensive research to develop medicines for stroke based on the known mechanisms either as glutamate receptor antagonists, Ca2+ channel blockers, enzyme inhibitors, inhibitors of apoptotic pathways, or ROS scavengers, etc., these efforts have been disappointing. Part of the reason for the disappointing results is due to the fact that the underpinning mechanism of stroke-induced neuronal injury is multi-factorial and hence it needs a therapeutic intervention that addresses the multi-factorial nature of the disease.

SUMMARY

It has been discovered that S-methyl-N, N-diethylthiolcarbamate sulfoxide (DETC-MeSO) is effective at protecting brain tissue exposed to a cerebral ischemia/reperfusion injury, and for minimizing the size of infarcts that develop as a result of the injury. It was also discovered that sulindac administration can protect brain tissue exposed to such an injury, and minize the size of infarcts that develop as a result of the injury. Also discovered was that the combination of granulocyte colony-stimulating factor (G-CSF; a stem cell enhancer and facilitator), DETC-MeSO, and sulindac can minimize the size of an infarct resulting from cerebral ischemia/reperfusion injury—even when each agent is administered at doses much lower (e.g., 10× lower) than required to observe a similar response using only one of the agents. This work also resulted in new information related to the molecular mechanisms by which these different agents can protect brain tissue exposed to ischemia/reperfusion.

These discoveries led to the development of a method for minimizing the size of a brain infarct which develops (or reducing the amount of brain tissue damaged) in a mammalian subject as a consequence of a cerebral ischemia/reperfusion injury. This method can include the step of administering to the subject at least one (e.g., 1, 2, or 3) of a DETC-MeSO agent, a G-CSF agent, and a sulindac agent, wherein the amount of the agent administered is effective for minimizing the size of a brain infarct that develops in a mammalian subject as a consequence of the cerebral ischemia/reperfusion injury. In this method, the subject can be who has been diagnosed with ischemic stroke prior to the administration step and/or one that has been administered tissue plasminogen activator or another thrombolytic. Combinations of two of DETC-MeSO agent, a G-CSF agent, and a sulindac agent might also be administered (e.g., a DETC-MeSO agent and a sulindac agent, a DETC-MeSO agent and a G-CSF agent, or a G-CSF agent and a sulindac agent), or all three can be administered. The at least one active ingredient can be included within a pharmaceutical composition formulated for injection, can be administered to the subject within 24 hours of the onset of symptoms of ischemic stroke, can be repeatedly administered to the subject at least once per day for at least 3 or at least 7 days or until the infarcted lesion becomes at least 50% fibrotic.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention provides methods and compositions for treating stroke, protecting brain tissue, and minimizing the size of a brain infarct caused by ischemia/reperfusion injury in a mammalian subject. The below described embodiments illustrate representative examples of these methods and compositions. Nonetheless, from the description of these embodiments, other aspects of the invention can be made and/or practiced based on the description provided below.

General Methods

Methods involving conventional organic chemistry, medicinal chemistry, pharmaceutical sciences, and drug development techniques are described herein. Such methods are described in: Remington: The Science and Practice of Pharmacy, Lippincott Williams & Wilkins, 21st edition (2005); Drug Discovery and Development, Mukund S. Chorghade (Editor) Wiley-Interscience; 1st edition (2007); The Practice of Medicinal Chemistry, 3rd Edition, Camille Georges Wermuth (Editor) Academic Press; 3rd edition (2008); and Clayden et al., Organic Chemistry, Oxford University Press, 1st edition (2000). Method in neurology are described in Bradley's Neurology in Clinical Practice, 6th Edition, Elsevier (2012).

Methods of Treating Ischemic Stroke

Methods of treating ischemic stroke and other ischemic neurologic injuries, or minimizing the size of a brain infarct caused by ischemia/reperfusion injury in a mammalian subject can include the step of administering one or more (e.g., 1, 2, or 3) of DETC-MeSO, G-CSF, and sulindac to the subject in an effective amount or amounts to minimize the size of a brain infarct resulting from the injury. Effective derivatives and analogues DETC-MeSO, G-CSF, and sulindac (including salts, epimers, and structurally related compounds of DETC-MeSO, G-CSF, and sulindac) might also be used in such methods. The G-CSF can be recombinant human G-CSF, or effective mutants, truncations, modifications (e.g., pegylated forms) thereof. The effectiveness of such derivatives and analogues can be confirmed by the methods described herein. Examples of such derivatives and analogues are described in U.S. Pat. Nos.: 3,654,349; 6,156,794; 7,414,139; 7,790,174 (and the relevant patent references cited therein); 8,044,048; and U.S. patent application Ser. No. 11/917,321. Each of the foregoing agents can be formulated as a separate pharmaceutical composition, or combinations of 2 or more (e.g., 2 or 3) of the foregoing agents can be formulated as a separate pharmaceutical composition.

The subject can be a mammal such as a human being, a rodent, a cat, a dog, a horse, a sheep, or a pig having or at risk for developing ischemic stroke or a brain infarct (e.g., a subject experiencing one or more transient ischemic attacks). As a non-limiting example, the subject can be a human being diagnosed with cerebral vessel occlusion or one having transient ischemic attacks. The subject can also be a human being who has been administered tissue plasminogen activator (e.g., following being diagnosed with acute cerebral vessel occlusion). The initial dose of one or more of DETC-MeSO, G-CSF, sulindac, or derivatives or analogues thereof can be administered within 1, 2, 3, 4, 5, 6, 7, 8, 9, 10, 11, 12, 13, 14, 15, 16, 17, 18, 19, 20, 24, 36, or 48 h of the onset of symptoms of ischemic stroke. For a subject at high risk for developing an ischemic stroke (e.g., subject experiencing transient ischemic attacks or having a thrombosis), the one or more of DETC-MeSO, G-CSF, sulindac, or derivatives or analogues thereof can be administered prophylactically, with a frequency of four times per day, thrice per day, twice per day, once a day, or once every 2, 3, 4, 5, 6, 7, or 14 days until the risk is decreased (e.g., transient ischemic attacks stop or the thrombosis is cleared).

The pharmaceutical formulation can be administered to the subject by any suitable method including orally, topically, by injection (e.g., intravenous, subcutaneous, intraperitoneal, or intrathecal injection; injection into an IV bag in fluid communication with a blood vessel in the subject; and infusion such as through a catheter), or implanting a slow-release depot device. For oral formulations, administrations can be, without limitation, four times per day, thrice per day, twice per day, once a day, or once every 2, 3, 4, 5, 6, 7, 14, 28, 35, 42, or 49 days (or until the ischemia/reperfusion-induced lesion becomes at least 50, 60, 70, 80, 90, or 100% fibrotic or acellular). For injectable formulations, administrations can be, without limitation, 100 µl to 100 ml (e.g., 100 µl, 500 µl, 1 ml, 2 ml, 3, ml, 4 ml, 5 ml, 10, ml, 20 ml, 50 ml, or 100 ml) four times per day, thrice per day, twice per day, once a day; or once every 2, 3, 4, 5, 6, 7, 14, 28, 35, 42, or 49 days (or until the ischemia/reperfusion-induced lesion becomes at least 50, 60, 70, 80, 90, or 100% fibrotic or acellular). Other possible methods of administration include intra-nasal (e.g., via a liquid spray, such as via a plastic bottle atomizer), inhalation or insufflation (e.g., of a dry powder formulation), and mucosal (rectal, vaginal, or buccal). Administration can continue indefinitely or until the infarct is completely formed or the factors causing an elevate risk for developing an ischemic stroke are removed. Brain lesions/infarcts can be monitored by methods known in the art, e.g., CT scanning.

The effective amount of the one or more of DETC-MeSO, G-CSF, sulindac, or derivatives or analogues thereof may be delivered in multiple doses, preferably within about three hours of the sudden onset of neurological symptoms associated with stroke. The effective amount of the one or more of DETC-MeSO, G-CSF, sulindac, or derivatives and analogues thereof may be delivered in combination with ongoing administration of aspirin to reduce the risk of blood clot formation, or administration of other agents to improve blood flow by reducing the formation of clots or dissolving blood clots (e.g., estrogen, eNOS inducer, L-arginine, a statin, aspirin, tissue plasminogen activator, modified viper venom, and prourokinase). In addition, agents and devices for controlling and regulating blood flow may also be used in combination with the one or more of DETC-MeSO, G-CSF, sulindac, or derivatives or analogues thereof to treat stroke or stroke-like events.

Pharmaceutical Formulations

The one or more active agents described herein can be included along with one or more pharmaceutically acceptable carriers or excipients to make pharmaceutical compositions which can be administered to the subject. Suitable formulations for use in the present invention are described in Remington's Pharmaceutical Sciences, Mace Publishing Company, Philadelphia, Pa., 17th ed. (1985) and updates thereto.

In pharmaceutical compositions including sulindac or derivatives or analogues of sulindac ("sulindac agents"), the sulindac agent can be included as at least 0.001% (e.g., at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0%) by weight of the formulation. Preferably the composition comprises between 0.001 to 3%, 0.005 to 2%, or 0.005 to 1.5% sulindac agent by weight. The dose of the sulindac agent per administration can be in the range of 0.01 to 5 mg/kg.

In pharmaceutical compositions including DETC-MeSO or derivatives or analogues of DETC-MeSO ("DETC-MeSO agents"), the DETC-MeSO agent can be included as at least 0.01% (e.g., at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, or 10%) by weight of the formulation. The dose of the DETC-MeSO agent agent per administration can be in the range of 0.2 to 20 mg/kg (preferably 1-10 mg/kg).

In pharmaceutical compositions including G-CSF or derivatives or analogues of G-CSF ("G-CSF agents"), the G-CSF agent can be included as at least 0.01% (e.g., at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, or 5%) by weight of the formulation. The dose of the DETC-MeSO agent per administration can be in the range of 2 to 500 µg/kg (preferably 10 to 100 µg/kg).

The pharmaceutical composition(s) might also be formulated for injection and administered by injection. Such compositions can have a pH of between 6.5 and 8.5 or between 6.8 and 7.8. Excipients/carriers/other ingredients can include a sterile aqueous buffer, an isotonizing agent, a microbicidal agent or preservative, a chelating agent, a solubility enhancing agent such as dimethylsulfoxide, and/or other ingredients. The isotonizing agent can be, e.g., sorbitol, glycerine, polyethylene glycol, propylene glycol, glucose and sodium chloride. The microbicidal agent/preservative can be, e.g., para-oxybenzoic acid esters, benzyl alcohol, para-chloro-meta-xylenol, chlorocresol, phenetyl alcohol, sorbic acid and salts thereof, thimerosal, chlorobutanol, etc. The chelating agent can be, for example, sodium edetate, sodium citrate or the sodium salt of condensed phosphoric acid.

The pharmaceutical composition can also be included in an implantable slow-release depot device that can be placed in the subject (e.g., at a subcutaneous position) by surgical techniques. In such devices, the one or more of DETC-MeSO, G-CSF, sulindac, or derivatives and analogues thereof can be manufactured into microparticles (e.g., with a particle size of 1 to 200 microns) which are embedded in a biocompatible pharmacologically acceptable polymer or a lipid encapsulating agent. The depot formulations can be designed to release all or substantially all the active material over an extended period of time, e.g. several weeks up to 6 months. The matrix, e.g. polymer or lipid matrix, if present, is adapted to degrade sufficiently to be transported from the site of administration within one to 6 months after release of all or substantially all the active agent.

To enhance half-life, the one or more of DETC-MeSO, G-CSF, sulindac, or derivatives and analogues thereof may be encapsulated, introduced into the lumen of liposomes, prepared as a colloid. A variety of methods are available for preparing liposomes, as described in, e.g., Szoka, et al., U.S. Pat. Nos. 4,235,871, 4,501,728 and 4,837,028 each of which is incorporated herein by reference. The one or more of DETC-MeSO, G-CSF, sulindac, or derivatives and analogues thereof may also be formulated for parenteral administration and presented in unit dosage form in ampules, prefilled syringes, small volume infusion containers or multi-dose containers with an added preservative.

EXAMPLES

Example 1

Stroke Model

Because most human focal ischemic strokes occur as a result of blockage of the middle cerebral artery, a proximal middle cerebral artery occlusion (MCAO) model was developed to evaluate the agents described herein. In the model, adult male Sprague-Dawley rats (250-300 g) are subjected to MCAO by inserting a filament and advancing 18-22 mm from the carotid artery bifurcation into the internal carotid artery. Reperfusion is accomplished by withdrawing the filament 2 h after MCAO. Cerebral blood flow (CBF) is measured during surgery until 30 min after reperfusion using the Laser Doppler flow (LDF) meter. In this procedure, LDF showed a marked reduction in CBF. The infarcts that formed were analyzed by triphenyltetrazolium chloride (TTC) staining of the brain.

Example 2

Effect of DETC-meSO Treatment on Stroke-Induced Brain Infarction.

DETC-MeSO at 1-7 mg was given two times: 1st injection given 1 hr before MCAO surgery and 2nd injection given on day 11. The animals were sacrificed on 11th day after ischemia induction. The brain was stained with 1% TTC. DETC-MeSO-treated animlas exhhited significantly reduced brain infarct size compared to the control group. In a second experiment, a quantitative analysis of infarct size with and without DETC-MeSO treatment was performed. For evaluation of the effects of DETC-MeSO animals were given 2 injections of the drug, one at 60 minutes before ischemia and one at 20 minutes before the start of reperfusion. After ischemia and reperfusion animals were sacrificed for determination of infarct size by TTC staining. Animals treated with DETC-MeSO demonstrated a decrease in infarct size to 29% the area of the infarcts in the no-drug control group.

Example 3

Effect of DETC-MeSO on Expression of C/EBP Homologues Protein (CHOP) in Primary Neuronal Cultures Subjected to Hypoxia and Reoxygenation.

Primary neuronal cultures were subjected to 24 hours of hypoxia followed by 16 hours of reoxygenation and cells were harvested for protein extraction and Western blot analysis for expression of CHOP. Levels of CHOP were quantified by densitometry and expressed as a percentage of the signal for actin control samples. Cells subjected to hypoxia demonstrated about double the of CHOP expression compared to both control cells (not subjected to hypoxia) and DETC-MeSO-treated cells subjected to hypoxia.

Example 4

Effect of DETC-MeSO on Expression of P-IRE-1 in Primary Neuronal Cultures Subjected to Hypoxia and Reoxygenation.

Primary neuronal cultures were subjected to 24 hours of hypoxia followed by 16 hours of reoxygenation and cells were harvested for protein extraction and Western blot analysis for expression of P-IRE-1. Levels of P-IRE-1 were quantified by densitometry and expressed as a percentage of the signal for actin control samples. Cells subjected to hypoxia demonstrated about 4-5 times the amount of P-IRE-1 expression compared to control cells (not subjected to hypoxia) and about 3-3.5 times the amount of P-IRE-1 expression compared to DETC-MeSO-treated cells subjected to hypoxia.

Example 5

Effect of a Combination of G-CSF/DETC-MeSO/Sulindac on Stroke-Induced Brain Infarction.

A combination of G-CSF/DETC-MeSO/sulindac at dose of G-CSF, 25 ug/kg; DETC-MeSO, 0.52 mg/kg; and sulindac, 1 mg/kg; was administered to animals 24 hrs post middle cerebral artery occlusion (MCAO) surgery in rat stroke model. Infarct size was reduced by approximately 40% compared to control animals (data from 14 experiments), when examined 8 days after MCAO surgery. Furthermore, ischemia-induced pro-apoptotic proteins (e.g., Bax and Bak) or ER stress proteins (e.g., GRP78) were reduced markedly at the infarct area to an extent of 55%, 88% and 62%, respectively in the animals receiving G-CSF/DETC-MeSO/sulindac compared to no-treatment controls. In addition, the anti-apoptotic protein Bcl2 increased greatly (437% at the core and 225% at the penumbra) in the animals receiving G-CSF/DETC-MeSO/sulindac compared to no-treatment controls.

Example 6

Effect of Sulindac on Stroke-Induced Brain Infarction.

Sulindac at 0.2 mg/kg reduced the brain infarct size when it was administered either before or post the middle cerebral artery occlusion (MCAO) surgery in the animal model described in Example 1. Specifically, animals with sham-operated or MCAO operated with or without sulindac treatment were sacrificed 3 and 11 days after stroke onset, and infarct size in the left hemisphere was measured by 2, 3, 5-triphenyltetrazolium chloride (TTC) staining. Western blotting on the core and the penumbra tissue of both hemispheres was employed for analysis of the expression of key proteins involved in apoptosis (Bcl-2), and cell protection and survival e.g., two heat shock proteins (HSP27, HSP70) and AKT. TTC analysis of brain slices indicated a decrease in infarct size in sulindac treated animals at 4 mm, 6 mm and 8 mm from the anterior pole. The Western blotting results indicated that Hsp 27 protein expression in ischemic penumbra and core on Day 3 and 11 was significantly increased in the sulindac-treated animals compared to the control non-treated animals. There were also significant increases in the protective molecules Akt and Bcl-2 in ischemic penumbra and core in the sulindac-treated animals compared to the control non-treated animals.

Example 7

DETC-MeSO as a Therapeutic Agent for Stroke Treatment.

DETC-MeSO is effective in reducing stroke-induced brain infarction administered either before or post to ischemic condition in the MCAO model described in Example 1. DETC-MeSO at 5.6 mg/kg was given one hour before MCAO surgery and reperfusion and then continued at the same dose for 4 days. The animals were sacrificed on 4th day after ischemia induction. The brain was stained with 1% TTC. DETC-MeSO significantly reduced brain infarct size at the dose specified. Quantitative analysis of infarct size with and without DETC-MeSO treatment was performed. After ischemia and reperfusion, the animals were sacrificed for determination of infarct size by TTC staining. Animals treated with DETC-MeSO demonstrated a decrease in infarct size by 50% at 6 mm from frontal pole compared with the area of the no-drug treated group. All data were expressed as the mean ±SEM (N=21). One-way ANOVA with post-hoc Dunnett test was used to compare means between groups. Differences of $P<0.05$ were considered statistically significant.

Example 8

Effect of DETC-MeSO Treatment Prior to MCAO Surgery and Reperfusion on the Expression of Bcl-2 and Hsp27 Proteins in the MCAO Stroke Animal Model.

Both Bcl-2 and Hsp-27 were found to be significantly increased in both the core and the penumbra region of the infarct brain tissue in the MCAO animals treated with DETC-MeSO compared to non-treated control animals. Western blots were quantified by densitometric analyses expressed as arbitrary unit. All data were expressed as the mean±SEM (N=8). Two-way ANOVA with post-hoc Bonferroni test (Prism software) was used to compare means between groups on core and penumbra with or without administration of DETC-MeSO. Differences of $P<0.05$ were considered statistically significant.

Example 9

Effect of DETC-MeSO Treatment Post MCAO Surgery.

DETC-MeSO at 5.6 mg/kg was given by intraperitoneal injection 24 hr post MCAO surgery/reperfusion and by continued daily injection at the same dose for additional 4 and 8 days until the animals were sacrificed. Morphological observation based on TTC staining shows that DETC-MeSO significantly reduced brain infarct size when it was administered 24 hrs post MCAO/reperfusion at the dose specified in both 4 and 8 days. Statistical analysis of the results obtained from 8 animals showed that DETC-MeSO treatment post MCAO surgery/reperfusion reduced ischemia—induced brain infarct size by 64+/−11% and 61+/−7% at 4- and 8-days respectively. The size of infarction of the DETC-MeSO-treated group was calculated as % of infarct area from the non-DETC-MeSO-treated group.

Example 10

G-CSF as an Effective Therapeutic Agent for Treatment of Stroke.

In the animal model described in Example 1, G-CSF administered 24 hours post ischemia at 50 µg/kg greatly reduced the ischemia-induced brain infarct size compared to non-treated control animals. The gross anatomy of brain sections (2 mm) was examined after TTC stain. Infarct volume was measured in brain slices at a distance of 2 mm interval from the frontal pole. Infarct volume and the percentage of infarct volume in entire brain was significantly reduced in G-CSF treated animals (n=5) versus the control group (n=5). (C) Percentage of infarct volume in entire brain of G-CSF treated animals (n=5) versus control group (n=5) (significance of $P<0.05$). Furthermore, it was demonstrated that the neuroprotective function of G-CSF is partially due to its up-regulation of endoplasmic reticular (ER) pro-survival/anti-apoptotic marker proteins (e.g., pAKT; JNK; and Bcl-2) or down-regulation of pro-apoptotic proteins (e.g., CHOP) by Western blotting as described above.

Example 11

Sulindac as a Therapeutic Agent for Stroke.

Sulindac administered via subcutaneous injection (0.2 mg/day) for 2 days before (Pre-MCAO Surgery/Reperfusion) and 24 hrs after ischemia (Post MCAO surgery/Reperfusion) in the animal described in Example 1, significantly reduced the infarct size induced by stroke compared to control non-treated animals. Quantitative analysis of TTC stained brain slices indicated a significant decrease in infarct size in sulindac treated animals at 4 mm, 6 mm, 8 mm and 10 mm from the anterior pole ($P<0.01$; 2 way ANOVA). In addition, the level of anti-apoptotic protein markers such as Bcl-2 was greatly elevated in sulindac-treated group compared to control non-treated animals.

Example 12

G-CSF/DETC-MeSO/Sulindac Combined Multi-drug Treatment for Stroke.

In the animal described in Example 1, it was found that G-CSF/DETC-MeSO/sulindac at dose of 1/10 of the individual drug (G-CSF, 10 ug/kg; DETC-MeSO, 0.56 mg/kg and sulindac, 0.2 mg/kg), reduced the infarct size significantly, approximately, 40%, when it was administered 24 hrs post MCAO surgery/reperfusion and examined at 8 days after MCAO/Reperfusion while individual drug at such a low concentration showed no significant effect on ischemia-induced infarct size. In a similar experiment, G-CSF/DETC-MeSO/sulindac at low dose (1/10 of the original individual drug used) (G-CSF, 10 ug/kg; DETC-MeSO, 0.56 mg/kg and sulindac, 0.2 mg/kg), reduced the infarct size significantly, approximately, 70%, when it was administered 24 hrs post MCAO surgery and examined at 4 days after MCAO/Reperfusion. Data represented infarct volume as percent (%) of the total ipsilateral hemisphere volume and are means ±SD of 9 experiments for MCAO and MCAO plus DETC-MeSO/GCSF/Sulindac combined multi-drug treatment.

Example 13

Experiment 2: Effect of G-CSF/DETC-MeSO/Sulindac Multi-drug Treatment Post MCAO on the Expression of ER Stress Proteins and Pro-apoptotic and Anti-apoptotic Proteins.

Ischemia-induced pro-apoptotic proteins (e.g., Bax, Bak) or ER stress proteins (e.g., GRP78) were reduced markedly at the infarct area to an extent of 55%, 88% and 62%, respectively, in animals administered G-CSF/DETC-MeSO/sulindac as described in Example 12 compared to no drug control animals. In addition, the anti-apoptotic proteins (e.g., Bcl-2) in both the infarct and penumbra regions was increased greatly to the extent of 437% and 225%, respectively. Western blots were quantified by densitometric analyses expressed as fold increase using the ipsilateral unlesioned side as the control. All data were expressed as the mean±SEM (N=8). Two-way ANOVA with post-hoc Bonferroni test (Prism software) was used to compare means between groups on core and penumbra with or without administration of G-CSF/DETC-MeSO/sulindac multi-drug treatment. Differences of $P<0.05$ were considered statistically significant.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a mammalian subject with acute cerebral vessel occlusion, the method comprising the step of administering to the subject a N-diethylthiocarbamate sulfoxide (DETC-MeSO) agent.

2. The method of claim 1, wherein the DETC-MeSO agent is administered to the subject within 24 hours of the onset of symptoms of cerebral vessel occlusion.

3. The method of claim 1, wherein the DETC-MeSO agent is repeatedly administered to the subject at least once per day for at least 3 days.

4. The method of claim 1, wherein the DETC-MeSO agent is repeatedly administered to the subject at least once per day for at least 7 days.

5. The method of claim 1, wherein the subject has been administered tissue plasminogen activator.

6. The method of claim 1, further comprising administering to the subject a sulindac agent.

7. The method of claim 1, further comprising administering to the subject a Granulocyte-colony stimulating factor (G-CSF) agent and a sulindac agent.

8. A method of preventing brain damage caused by ischemic stroke in a mammalian subject experiencing transient ischemic attacks, the method comprising the step of administering to the subject a N-diethylthiocarbamate sulfoxide (DETC-MeSO) agent.

9. The method of claim 8, wherein the DETC-MeSO agent is repeatedly administered to the subject until the transient ischemic attacks stop.

10. A method of preventing brain damage caused by ischemic stroke in a mammalian subject having a thrombosis, the method comprising the step of administering to the subject a N-diethylthiocarbamate sulfoxide (DETC-MeSO) agent.

11. The method of claim 10, wherein the DETC-MeSO agent is repeatedly administered to the subject until the thrombosis is cleared.

* * * * *